(12) United States Patent
Rautenstrauch et al.

(10) Patent No.: US 7,317,131 B2
(45) Date of Patent: Jan. 8, 2008

(54) CATALYTIC HYDROGENATION PROCESSES

(75) Inventors: Valentin Rautenstrauch, Collonges-sous-Saleve (FR); René Challand, Geneva (CH); Raphaël Churlaud, Le Mans (FR); Robert Harold Morris, Toronto (CA); Eric Brazi, Thoiry (FR); Hubert Mimoun, Challex (FR); Kamaluddin Abdur-Rashid, Mississauga (CA)

(73) Assignee: Firmenich SA, Geneva (CH)

( * ) Notice: Subject to any disclaimer, the term of this patent is extended or adjusted under 35 U.S.C. 154(b) by 743 days.

(21) Appl. No.: 10/380,483

(22) PCT Filed: Sep. 11, 2001

(86) PCT No.: PCT/IB01/01657

§ 371 (c)(1),
(2), (4) Date: Sep. 3, 2003

(87) PCT Pub. No.: WO02/22526

PCT Pub. Date: Mar. 21, 2002

(65) Prior Publication Data

US 2004/0063966 A1    Apr. 1, 2004
US 2005/0245748 A9    Nov. 3, 2005

Related U.S. Application Data

(60) Provisional application No. 60/232,144, filed on Sep. 13, 2000.

(51) Int. Cl.
*C07C 29/14* (2006.01)

(52) U.S. Cl. .................. 568/881; 568/814; 568/850

(58) Field of Classification Search ................ 568/881, 568/814, 850
See application file for complete search history.

(56) References Cited

U.S. PATENT DOCUMENTS 5,780,692 A * 7/1998 Sakaguchi et al. .......... 568/814
6,878,852 B2 * 4/2005 Rautenstrauch et al. .... 568/881

FOREIGN PATENT DOCUMENTS

| EP | 0 718 265 B1 | 6/1996 |
| EP | 0 780 157 B1 | 6/1997 |
| EP | 0 901 997 B1 | 3/1999 |
| EP | 0 916 637 A1 | 5/1999 |
| EP | 1 013 658 A  | 6/2000 |

OTHER PUBLICATIONS

Jingxing Gao, "Preparation of chiral diaminodiphosphine metal complexes as catalysts in asymmetrically catalytic hydrogenation", Chemical Abstract, vol. 132, No. 7, pp. 1463 (2000).

Abdur Rashid et al., Ruthenium Dihydride, Ru $H_2(PPh_3)_2$(R,R)-cyclohexyldiamine) and Ruthenium Monohydride $RuHCl(PPh_3)_2$(R,R)- )-cyclohexyldiamine: Active Catalyst and Catalyst Precursor for the Hydrogenation of Ketones and Imines, American Chemical Society, Organometallics, vol. 19, pp. 2655-2657 (2000).

Noyori et al., Asymmetric Catalysis by Architectural and Functional Molecular Engineering: Practical Chemo-and Stereoselective Hydrogenation of Ketones, Angew. Chem. Int Ed. vol. 40, pp. 40-73 (2001).

* cited by examiner

*Primary Examiner*—Rei-tsang Shiao
(74) *Attorney, Agent, or Firm*—Winston & Strawn LLP

(57) ABSTRACT

The catalysts of formula (II): $[Ru(L)_m(L')_wXY]$, wherein X and Y represent simultaneously or independently a hydrogen or halogen atom, a hydroxy group, or an alkoxy, carboxyl or other anionic radical, m is 1 or 2, w is 1 when m is 1 and w is 0 when m is 2, L is a phosphino-amine or phosphino-imine bidentate ligand and L' a diphosphine, are useful for the hydrogenation of substrates having a carbon-hetero atom double bond.

17 Claims, No Drawings

CATALYTIC HYDROGENATION PROCESSES

CROSS-REFERENCE TO RELATED APPLICATIONS

This application is a 371 filing of International Application PCT/IB01/01657 filed Sep. 11, 2001, which claims the benefit of International Application PCT/IB00/01303 filed Sep. 13, 2000 and of U.S. provisional application 60/232,144 filed Sep. 13, 2000.

TECHNICAL FIELD

The present invention relates to the field of catalytic hydrogenation and, more particularly, to the use of metal complexes with P—N bidentate ligands in hydrogenation processes for the reduction of compounds containing a carbon-heteroatom double bond.

PRIOR ART

Reduction of carbon-heteroatom double bond groups such as ketone, aldehyde or imine groups, is one of the fundamental reactions in chemistry, and is used in a large number of chemical processes.

Several different kinds of processes are known to achieve such transformation, and they can be classified in four main types according to the nature of the reducing system:
a) enzymatic processes, in which an enzyme is used to catalyze the reduction
b) hydride processes, in which a hydride metal salt such as $LiAlH_4$ is used
c) hydrogen transfer processes, in which hydrogen-donors such as secondary alcohols and in particular isopropanol ($^i$PrOH) are used
d) hydrogenation processes, in which molecular hydrogen is used.

However, from a practical point of view, the industrial application of the first two methods is difficult since the use of enzymes is delicate and can limit the structure of the compound that can be reduced. On the other hand, hydride processes require the use of highly reactive, hazardous and expensive hydrides.

Both hydrogen transfer and hydrogenation processes need a catalyst or catalytic system (e.g. a pre-catalyst) to activate the reducing agent, namely an alcohol or molecular hydrogen respectively.

Despite the fact that many catalysts for the reduction of a carbon-heteroatom double bond by hydrogen transfer are already known, hydrogen transfer processes are still of difficult application for industrial purposes since they need very large volumes of solvents as reducing agents and high catalyst loadings.

From a practical point of view, hydrogenation processes are more attractive as they use cheap hydrogen gas and can be run out in the presence of a small quantity or even in the absence of solvent, in contrast to the hydrogen transfer processes, which need large volumes of solvent as reductant. However, the former process implies the activation of molecular hydrogen, which is more difficult to achieve than the activation of an alcohol.

For a long time the development of useful catalysts for the hydrogenation of carbon-heteroatom double bonds has been an unachieved goal in chemistry, and it was only recently that several new catalysts for the hydrogenation of ketones have been developed.

The hydrogenation catalysts for simple ketones reported up to now have the same general formula, always including a ruthenium atom coordinated by a bidentate ligand and two monodentate phosphines or amines, or two bidentate ligands. The bidentate ligands are always a diphosphine (P—P) or a diamine (N—N), and the metal centre is always coordinated to two phosphorous atoms and two nitrogen atoms. Very efficient pre-catalysts are those of the formula $[Ru(P—P)(N—N)Cl_2]$ (see R. Noyori et al., in *Angew. Chem.Int.Ed.*, 2001, 40, 41; Morris et al. in *Organometallics*, 2000, 19, 2655; or Takasago EP 0901997 and JP 11189600).

From the examples cited herein above, one can notice that the catalysts reported up to now exhibit little diversity of the ligand structure and coordination spheres around the metal center. As a consequence of such little diversity, the tuning of the activity and of the performance of the hydrogenation process is not easy. Additionally, these catalysts generally need the use of ligands such as BINAP or sophisticated chiral diamines which require themselves a long, difficult and tedious synthesis.

Therefore, there is a need for hydrogenation processes using catalysts or pre-catalysts with a greater diversity in the ligand structures and coordination spheres around the metal center, and implying the use of ligands that are easily and readily obtained.

DESCRIPTION OF THE INVENTION

In order to overcome the problems aforementioned, the present invention relates to new processes for the reduction by hydrogenation of compounds containing a carbon-heteroatom double bond wherein metal complexes with P—N bidentate ligands are usefully used as catalysts or as pre-catalysts.

The invention concerns a process for the hydrogenation, using molecular hydrogen ($H_2$), of a C=O or C=N double bond of a substrate into the corresponding hydrogenated compound, in the presence of a catalyst or pre-catalyst (hereinafter referred to as "complex" unless specified otherwise) and a base.

More particularly, typical substrates that can be reduced by the process of the invention are of formula

(I)

wherein W is an oxygen atom or a NR group, R being a hydrogen atom, a hydroxy radical, a $C_1$ to $C_8$ cyclic, linear or branched alkyl or alkenyl group, possibly substituted, or an aromatic ring, possibly substituted; and $R^a$ and $R^b$ represent simultaneously or independently a hydrogen, an aromatic group possibly substituted, a cyclic, linear or branched alkyl or alkenyl group, possibly substituted, or a heterocyclic group possibly substituted; or two of symbols $R^a$, $R^b$ and R, taken together, form a ring, possibly substituted, and provide the corresponding hydrogenated compound of formula

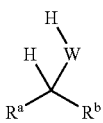

wherein W, $R^a$ and $R^b$ are defined as in formula (I).

Possible substituents of $R^a$, $R^b$ and R are halogen atoms, $OR^c$, $NR^c_2$ or $R^c$ groups, in which $R^c$ is a hydrogen atom or a $C_1$ to $C_{10}$ cyclic, linear or branched alkyl or alkenyl group.

Since $R^a$ and $R^b$ may be different, it is hereby understood that the final product of formula (I') may be chiral, thus possibly consisting of a practically pure enantiomer or of a mixture of stereoisomers, depending on the nature of the catalyst used in the process.

Preferred substrates are the imines (W=NR), ketones or aldehydes (W=O) that will provide respectively an amine or alcohol, which are useful in the pharmaceutical, agrochemical or perfumery industries as final product or as an intermediate.

Particularly preferred substrates are the ketones or aldehydes that will provide an alcohol which is useful in the perfumery industry, as final product or as an intermediate. Also particularly preferred substrates are the imines that will provide an amine, particularly useful in the pharmaceutical or agrochemical industries, again as final product or as an intermediate.

The processes of the invention are characterized by the use of a complex of the general formula

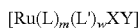

wherein X and Y represent, simultaneously or independently, a hydrogen or halogen atom, a hydroxy radical, or a $C_1$ to $C_8$ alkoxy or acyloxy radical;

m is 1 or 2, w is 1 when m is 1 and w is 0 when m is 2;

L represents a bidentate N—P ligand of general formula

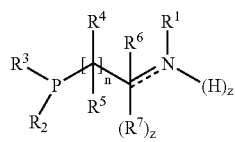

in which formula (III) the dotted line indicates a single or double bond;

n is an integer from 1 to 4; z is 0 or 1 when the carbon-nitrogen bond with the dotted line represents a double, respectively single bond;

$R^1$ represents a hydrogen atom, a linear, branched or cyclic $C_1$ to $C_{10}$ alkyl or alkenyl group, possibly substituted, a R*CO acyl group, or a R*SO$_2$ group, R* representing a $C_1$ to $C_8$ alkyl or aryl group;

$R^2$ and $R^3$ represent, simultaneously or independently, a linear, branched or cyclic $C_1$ to $C_8$ alkyl or alkenyl group, possibly substituted, an aromatic ring, possibly substituted, or an $OR^{2'}$ or $NR^{2'}R^{3'}$ group, $R^{2'}$ and $R^{3'}$ being defined as $R^2$ and $R^3$; or said groups $R^2$ and $R^3$ being possibly bonded together to form a saturated or aromatic ring having 5 to 10 atoms and including the phosphorous atom to which said $R^2$ and $R^3$ groups are bonded;

$R^4$, $R^5$, $R^6$ and $R^7$ represent, simultaneously or independently, a hydrogen atom, a linear, branched or cyclic $C_1$ to $C_{10}$ alkyl or alkenyl group, possibly substituted, an aromatic ring, possibly substituted, or an $OR^{4'}$ or $NR^{4'}R^{5'}$ group, $R^{4'}$ and $R^{5'}$ being defined as $R^4$ and $R^5$; or two distinct $R^4$ and/or $R^5$ groups being possibly bonded together to form a $C_5$ to $C_8$ saturated or aromatic ring including the carbon atoms to which each of said $R^4$ or $R^5$ group is bonded; or $R^6$ and $R^1$ may optionally be bonded together to form a saturated or unsaturated heterocycle, possibly substituted and possibly containing other heteroatoms, having 5 to 10 atoms and including the carbon atom and the N atom of the bond indicated by the dotted line; and L' represents a bidentate P—P ligand of formula

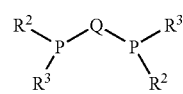

wherein $R^2$ and $R^3$ are defined as in formula (III), and Q represents a linear or cyclic $C_2$-$C_7$ alkylene radical, possibly substituted, a metallocenediyl or a $C_6$-$C_{22}$ arylene or biaryldiyl radical, possibly substituted.

Possible substituents of $R^1$ to $R^7$ and Q are $C_1$ to $C_{10}$ alkoxy or polyalkyleneglycol groups, carboxylic esters, $C_1$ to $C_6$ alkyl groups, or $C_5$ to $C_{12}$ cycloalkyl or aromatic groups.

The ligands L and L' may be chiral or achiral. Therefore, the invention may provide complexes of formula (II) useful in asymmetric hydrogenations.

In a preferred embodiment of formula (II), X and Y represent, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical;

m is 1 or 2, w is 1 when m is 1 and w is 0 when m is 2;

L represents a bidentate N—P ligand of general formula

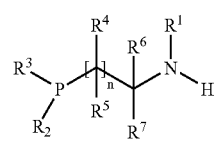

in which n is an integer from 1 to 3;

$R^1$ represents a hydrogen atom, a linear, branched or cyclic $C_1$ to $C_6$ alkyl or alkenyl group, possibly substituted;

$R^2$ and $R^3$ represent, simultaneously or independently, a linear, branched or cyclic $C_2$ to $C_6$ alkyl group, possibly substituted, an aromatic ring, possibly substituted; or said groups $R^2$ and $R^3$ being possibly bonded together to form a saturated or aromatic ring having 5 to 6 atoms and including the phosphorous atom to which said $R^2$ and $R^3$ groups are bonded;

$R^4$, $R^5$, $R^6$ and $R^7$ represent, simultaneously or independently, a hydrogen atom, a linear or branched $C_1$ to $C_4$ alkyl group, possibly substituted, or an aromatic ring possibly substituted; or two distinct $R^4$ and/or $R^5$ groups being possibly bonded together to form a $C_5$ to $C_6$ saturated or aromatic ring including the carbon atoms to which each of said $R^4$ or $R^5$ group is bonded; or $R^6$ and $R^1$ may optionally be bonded together to form a saturated heterocycle, possibly substituted and possibly containing other heteroatoms, having 5 to 6 atoms and including the carbon atom and the N atom of the bond indicated by the dotted line; and L' represents a bidentate P-P ligand of formula (IV) wherein $R^2$ and $R^3$ are defined as in formula (III'), and Q represents a linear $C_2$-$C_5$ alkylene radical, possibly substituted, a ferrocenediyl or a biphenyldiyl or binaphthyldiyl radical, possibly substituted.

Possible substituents of $R^1$ to $R^7$ and Q are $C_1$ to $C_5$ alkoxy or polyalkyleneglycol groups, carboxylic esters, $C_1$ to $C_4$ alkyl groups, or $C_5$ to $C_{10}$ cycloalkyl or aromatic groups.

In an alternative preferred embodiment of the complexes of formula (II), X and Y represent, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical;

m is 1 or 2, w is 1 when m is 1 and w is 0 when m is 2;

L represents a bidentate N—P ligand of general formula

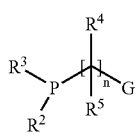

(III")

in which G represents a group of formula $R^6C=NR^1$ or a C=N function-containing heterocycle, possibly substituted and possibly containing other heteroatoms, such as a 2-pyridyl, a 1-oxazolinyl, a 2-imidazolyl or a 2-isoquinolinyl group;

$R^6$ represents a hydrogen atom, a linear or branched $C_1$ to $C_4$ alkyl group, possibly substituted, or an aromatic ring possibly substituted;

n, $R^1$, $R^2$, $R^3$, $R^4$, $R^5$ are defined as in formula (III'); and

L' represents a bidentate P—P ligand of formula (IV) wherein $R^2$ and $R^3$ are defined as in formula (III'), and Q represents a linear $C_2$-$C_5$ alkylene radical, possibly substituted, a ferrocenediyl or a biphenyldiyl or binaphthyldiyl radical, possibly substituted.

Possible substituents of $R^1$ to $R^6$, Q and G are $C_1$ to $C_5$ alkoxy or polyalkyleneglycol groups, carboxylic esters, $C_1$ to $C_4$ alkyl groups, or $C_5$ to $C_{10}$ cycloalkyl or aromatic groups.

Particularly advantageous when used in the processes of the invention are the complexes of formula

[Ru(L)$_2$XY]  (II')

wherein X and Y represent, simultaneously or independently, a hydrogen or chlorine atom, a methoxy, ethoxy or isopropoxy radical, or a $CH_3COO$ or $CH_3CH_2COO$ radical; and L is a ligand of formula (V) or (V')

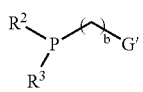

(V)

-continued

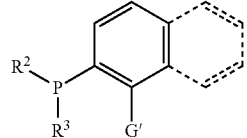

(V')

wherein the dotted lines in formula (V') indicate the presence of a phenyl or a naphthyl group;

b represents 1 or 2;

G' represents a $R^6C=NR^1$ group or a C=N function-containing heterocycle, possibly substituted and possibly containing other heteroatoms, such as a 2-pyridyl, an 2-isoquinolinyl, an 1-oxazolinyl, or a 2-imidazolyl group;

$R^1$ represents a hydrogen atom or a $C_1$ to $C_4$ linear or branched alkyl group, possibly substituted;

$R^2$ and $R^3$ represent a linear, branched or cyclic $C_2$ to $C_6$ alkyl group or an aromatic ring, possibly substituted; and $R^6$ represents a hydrogen atom, a linear or branched $C_1$ to $C_4$ alkyl group, possibly substituted, or an aromatic ring, possibly substituted.

Possible substituents of $R^1$ to $R^3$, $R^6$ and G' are $C_1$ to $C_5$ alkoxy or polyalkyleneglycol groups, $C_1$ to $C_4$ alkyl groups, or $C_5$ to $C_{10}$ cycloalkyl or aromatic groups.

In an alternative embodiment of the complexes of formula (II'), L is a ligand of formula (VI) or (VI')

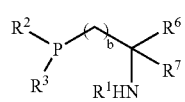

(VI)

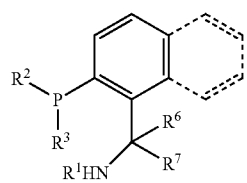

(VI')

wherein the dotted lines in formula (VI') indicate the presence of a phenyl or a naphthyl group;

$R^1$, $R^2$, $R^3$, and b are defined as in formula (V) or (V'); and $R^6$ and $R^7$ represent, simultaneously or independently, a hydrogen atom, a linear or branched $C_1$ to $C_4$ alkyl group, possibly substituted, or an aromatic ring possibly substituted; or $R^6$ and $R^1$ may optionally be bonded together to form a saturated heterocycle, possibly substituted and possibly containing other heteroatoms, such as a 2-pyrrolidine, a 2-piperidine or a 2-morpholine heterocycle.

Possible substituents of $R^1$ to $R^3$, $R^6$ and $R^7$ are $C_1$ to $C_5$ alkoxy or polyalkyleneglycol groups, $C_1$ to $C_4$ alkyl groups, $C_5$ to $C_{10}$ cycloalkyl or aromatic groups.

Moreover, in the processes of the invention, it is possible to use in a particularly advantageous manner the complexes of formula

[Ru(L)$_1$(L')$_1$XY]  (II")

wherein X and Y represent, simultaneously or independently, a hydrogen or chlorine atom, a methoxy, ethoxy or isopropoxy radical, or a $CH_3COO$ or $CH_3CH_2COO$ radical;

L' is a bidentate P—P ligand of formula (IV) wherein $R^2$ and $R^3$ are defined as in formula (V), and Q represents the butane-1,4-diyl radical, possibly substituted, a ferrocenediyl or a binaphthyldiyl radical, possibly substituted; and L is a ligand of formula (VI) or (VI').

Possible substituents of Q are $C_1$ to $C_5$ alkoxy or polyalkyleneglycol groups, $C_1$ to $C_4$ alkyl groups, or $C_5$ to $C_{10}$ cycloalkyl or aromatic groups.

In an alternative preferred embodiment of the complexes of formula (II"), L is a ligand of formula (V) or (V').

The complexes of formula (II') or (II") are, to the best of our knowledge, new compounds and therefore are also part of the invention.

Many of the ligands described above are known in the art and, unless specified differently in the examples, they are obtained according to methods described in the literature. The ligands that are new can be obtained by modifying known procedures according to the general knowledge of a person skilled in the art. Some references are cited in the examples.

The complexes used in the processes of the invention can be prepared in situ in the hydrogenation reaction medium, without isolation or purification, just before their use. Alternatively, they can be isolated before use. The experimental procedure for their synthesis is substantially similar in both cases. Furthermore, they can also be prepared and stored in solution, the latter being stable for many days.

Said complexes can be prepared according to methods similar to those described in the literature, e.g. by Noyori et al. in JP 11189600, or in *Angew. Chem. Int. Ed.* 1998, 37, 1703-1707, or by Yang et al. in *C.R.Acad.Sci., Ser.IIc: Chim.* 1999, 2, 251, or yet by Quirmbach et al. in *Tetrahedron*, 2000, 56, 775

As previously mentioned, the complexes can be prepared in situ, in the hydrogenation medium, by several methods without isolation or purification, just before their use. We have established that one of the possible procedures to advantageously prepare in situ a complex of formula (II) consists in reacting an appropriate Ru complex of formula

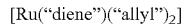

in which "diene" represents a cyclic or linear hydrocarbon containing two carbon-carbon double bonds, conjugated or not, such as for example 1,5-cyclooctadiene (COD) or 1,3-butadiene, and "allyl" represents a linear or branched $C_3$ to $C_8$ hydrocarbon radical containing one carbon-carbon double bond, such as for example the allyl ($CH_2CHCH_2$) or methylallyl ($CH_2CCH_3CH_2$) group, with a non-coordinating acid such as $HBF_4.Et_2O$, preferably one equivalent in respect to the metal, then treating the resulting solution with the desired amount of a ligand L, and if necessary of ligand L', as defined previously, and finally treating the thus obtained mixture with a base in the presence of a primary or secondary alcohol.

Preferably the [Ru(diene)(allyl)$_2$] is [Ru(COD)(allyl)$_2$] or [Ru(COD)(methylallyl)$_2$].

Another procedure to advantageously prepare in situ a complex of formula (II) consists in reacting a ruthenium complex of formula [Ru(C$_6$H$_6$)(Cl)$_2$]$_2$ with a required amount of ligand L, and if necessary of ligand L', as defined previously, and then treating the thus obtained reaction mixture with a base, in the presence of an alcohol.

In any case, and independently of the procedure chosen to prepare the complex in situ, the base used is, preferably, the same base used in the process of the invention.

As previously mentioned, the complexes of formula (II), (II') or (II") are very useful for the reduction by hydrogenation of compounds containing a carbon-heteroatom double bond. A typical process implies the mixture of the substrate with a complex of formula (II), (II') or (II"), in the presence of a base and optionally a solvent, and then treating such a mixture with molecular hydrogen at a chosen pressure and temperature.

The complexes used in the processes of the invention, an essential parameter of the process, can be added to the reaction medium in a large range of concentrations. As non-limiting examples, one can cite as complex concentration values ranging from 0.1 ppm to 50000 ppm, relative to the amount of substrate, thus representing respectively a substrate/complex (S/com) ratio of $10^7$ to 20. Preferably, the complex concentration will be comprised between 0.1 and 5000 ppm, i.e. a S/com ratio of $10^7$ to 200 respectively. More preferably, there will be used concentrations in the range of 0.5 to 1000 ppm, corresponding to a S/com ratio of $2\times10^6$ to 1000 respectively. It goes without saying that the optimum concentration of complex will depend on the nature of the latter and on the pressure of $H_2$ used during the process.

As mentioned previously the process of the invention is performed in the presence of a base.

Said base can be the substrate itself, if the latter is basic, or any conventional base. One can cite, as non-limiting examples, organic non-coordinating bases such as DBU, an alkaline or alkaline-earth metal carbonate, a carboxylate salt such as sodium or potassium acetate, or an alcoholate or hydroxide salt. Preferred bases are the alcoholate or hydroxide salts selected from the group consisting of the compounds of formula $(R^8O)_2M'$ or $R^8OM"$, wherein M' is an alkaline-earth metal, M" is an alkali metal and $R^8$ stands for hydrogen or a $C_1$ to $C_6$ linear or branched alkyl radical.

Useful quantities of base, added to the reaction mixture, may be comprised in a relatively large range. One can cite, as non-limiting examples, ranges comprised between 0.5 to 90000 molar equivalents, relative to the complex (e.g. base/complex=0.5 to 90000), preferably 5 to 10000, and even more preferably between 10 and 5000 molar equivalents. However, it should be noted that, depending on the substrate and the complex structure, it is also possible to add a small amount of base (e.g. base/complex=1 to 5) to achieve high hydrogenation yields.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or mixtures thereof. A person skilled in the art is well able to select the solvent most convenient in each case to optimize the hydrogenation reaction, however primary or secondary alcohols such as ethanol or isopropanol are the preferred solvents.

In the hydrogenation processes of the invention, the reaction can be carried out at a $H_2$ pressure comprised between $10^5$ Pa and $80\times10^5$ Pa (1 to 80 bars). Again, a person skilled in the art is well able to adjust the pressure as a function of the catalyst load and of the dilution of the substrate in the solvent. As examples, one can cite typical pressures of 1 to $40\times10^5$ Pa (1 to 40 bar).

The temperature at which the hydrogenation can be carried out is comprised between 0° C. and 100° C., more preferably in the range of between 20° C. and 40° C. Of course, a person skilled in the art is also able to select the preferred temperature as a function of the melting and boiling point of the starting and final products or of the solvent if present.

Additionally, we surprisingly discovered that in some cases it is possible to successfully hydrogenate some substrates into the corresponding alcohols in the presence of hydrido or diacetato complexes of formula (II'), without a base.

Therefore, the invention concerns also a process for the reduction of an aryl or diaryl ketone into the corresponding alcohol by hydrogenation in the presence of a complex, said process being characterized in that said complex is of formula:

[Ru(L)$_2$XY]     (II')

wherein L is as ligand of formula (V), (V'), (VI) or (VI'); and X represents a hydrogen atom and Y represents a hydrogen or chlorine atom, a methoxy, ethoxy or isopropoxy radical, or a CH$_3$COO or CH$_3$CH$_2$COO radical; or X and Y represent a hydrogen atom or a CH$_3$COO or CH$_3$CH$_2$COO radical.

Said processes are typically performed by admixing the substrate with a complex of formula (II'), as herein above defined, optionally in presence a solvent, and then treating such a mixture with molecular hydrogen at a chosen pressure and temperature. The concentration of the complex relative to the substrate, the nature of the optional solvent, the H$_2$ pressure and the temperature of the process are as previously described.

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave or in Schlenk flasks. H$_2$ gas (purity: 99.99% or more) was used as received. All substrates and solvents were distilled from appropriate drying agents under Ar. NMR spectra were recorded on Bruker instruments ($^1$H at 400.1 MHz, $^{13}$C at 100.6 MHz, and $^{31}$P at 121.4, 145.8 or 161.9 MHz) and normally measured at 300 K Chemical shifts are listed in ppm.

EXAMPLE 1

Preparation of some Ru Complexes of the Formula (II)

TABLE 1

Structure of the ligands of formula (IV) or (VI) used for the synthesis of the corresponding complexes

| structure | name |
|---|---|
| 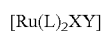 H$_2$N⁀PPh$_2$ | (VI)-1 |
| H$_2$N⁀PPh$_2$ | (VI)-2 |

TABLE 1-continued

Structure of the ligands of formula (IV) or (VI) used for the synthesis of the corresponding complexes

| structure | name |
|---|---|
| C$_6$H$_{11}$ H$_2$N⁀PPh$_2$ | (VI)-3 |
| Fc(Cp-PPh$_2$)(Cp-PPh$_2$) | (IV)-1 |
| BINAP (PPh$_2$/PPh$_2$) | (IV)-2 |
| DIOP (O O PPh$_2$/PPh$_2$) | (IV)-3 |

Ligand (VI)-1 is commercially available from FLUKA.
Ligands (VI)-2 and (VI)-3 were obtained from the corresponding aminoacids according to the procedure described in K. Kashiwabara, et.al.; Bull. Chem. Soc. Jpn., 1981, 54, 725; S. Sakuraba, et. al.; Chem. Pharm. Bull., 1995, 43, 927; A. Saitoh, et.al.; Synlett., 1999, 4, 483; A. Saitoh, et. al.; J. Org. Chem., 2000, 65, 4227.
Ligands (IV)-1, 2, 3 are commercially available from Aldrich Chemical Company a) Preparation of the Complex [RuHCl((VI)-1)$_2$]:

Isopropanol (5 ml) was added to a mixture of [RuCl$_2$(COD)]$_n$ (300 mg, 1.07 mmol of Ru), NaOH (200 mg, 5.0 mmol) and (VI)-1 (510 mg, 2.2 mmol) under a flow of argon, and the resulting suspension stirred for 6 hours, during which a bright yellow precipitate formed. Water (30 ml) was added and the mixture was stirred for another hour. It was then filtered using a schlenk sintered glass frit, washed with water (3×10 ml) and vacuum dried. Recrystallization from toluene/hexanes afforded a pure sample of the complex. Yield=386 mg, 60%.

$^1$H NMR (C$_6$D$_6$): −19.83(t, $^2$J$_{HP}$=25.9 Hz, 1H, RuH); 2.18-4.54(m, 12H); 6.90-7.38(m, 20H, Ph). $^{31}$P{$^1$H} NMR (C$_6$D$_6$): 77.8(s). IR (Nujol): 1924 cm$^{-1}$ (νRuH), 3282, 3141 cm$^{-1}$(νNH).

b) Alternative Preparation of the Complex [RuHCl((VI)-1)$_2$]:

A solution of [RuHCl(Ph$_3$P)$_3$] (obtained as described by Schunn et al. in Inorg.Synth., 1970, 131) (1002 mg, 1.00 mmol) and (VI)-1 (458 mg, 2.00 mmol) in toluene (40 mL) was stirred and heated to 40° C. for 24 h and then for another 2 h at 100° C. Then, about half of the solvent was stripped off under vacuum from the yellow suspension, and the yellow precipitate then directly collected by filtration at ambient temperature. The filtrate was washed with pentanes and dried in vacuum to give 520 mg of [RuHCl(VI)-1)$_2$] (0.87 mmol, yield=87%).

$^1$H NMR (d$_8$-THF): −19.3 ppm (t, J=26.4 Hz, hydride); $^1$H NMR (d$_6$-DMSO): −10.9 ppm (t, J=25.2 Hz, hydride); $^{31}$P{$^1$H} NMR (d$_8$-THF): 83.2 ppm (s); $^{31}$P{$^1$H} NMR (d$_6$-DMSO): 71.9 ppm (s).

c) Preparation of the Complex [RuCl$_2$((VI)-1)$_2$]:

A 50 mg sample of [RuHCl((VI)-1)$_2$] was dissolved in methylene chloride (1.0 ml) and the resulting solution was allowed to stand at room temperature for 24 hours. A bright yellow precipitate was obtained upon addition of diethyl ether (2 ml). Yield=43 mg, 81%.

$^1$H NMR (CD$_2$Cl$_2$): 1.68-3.72 (m, 12H); 6.99-7.17 (m, 20H, Ph). $^{31}$P {$^1$H} NMR (CD$_2$Cl$_2$): 62.51 (s).

d) Alternative Preparation of the Complex [Ru(Cl)$_2$((VI)-1)$_2$]:

Toluene (5 ml) was added to a mixture of [RuCl$_2$(COD)]$_n$ (300 mg, 1.07 mmol) and (VI)-1 (510 mg, 2.2 mmol) and the resulting suspension refluxed for 12 hours under argon, during which a bright yellow precipitate formed. The mixture was cooled to room temperature and the solids filtered, washed with toluene (3×5 ml), then ether (3×5 ml) and vacuum dried. Yield=582 mg, 91%.

$^1$H NMR (CD$_2$Cl$_2$): 1.68-3.72 (m, 12H), 6.99-7.17 (m, 20H, Ph). $^{31}$P{$^1$H} NMR (CD$_2$Cl$_2$): 62.51.

e) Preparation of the Complex [RuHCl((VI)-2)$_2$]:

This complex was prepared using a similar procedure to that described in a) or in b).

Yield=67% for method a).

$^1$H NMR (CD$_6$): −19.15 (t, $^2$J$_{HP}$=25.4 Hz, 1H, RuH); 1.01-4.54 (m, 16H); 6.93-7.76(m, 20H, Ph). $^{31}$P {$^1$H} NMR (C$_6$D$_6$): 72.9(d), 72.4(d, $^2$J$_{PP}$=34.8 Hz).

f) Preparation of the Complex [RuCl$_2$((VI)-2)$_2$]:

This complex was prepared using a similar procedure to that described in d) or in c). Yield=83% for method c.

$^1$H NMR (C6D$_6$): 1.01-3.68(m, 16H); 6.87-62(m, 20H, Ph). $^{31}$P{$^1$H} NMR(C$_6$D$_6$): 57.5(s).

g) Preparation of the Complex [RuHCl((VI)-3)$_2$]:

This complex was prepared using a similar procedure to that described in a) or in b) and resulted in a mixture of diastereomers. However, the isolated solid was effectively used as a catalyst precursor in the ketone hydrogenation.

h) Preparation of the Complex [RuHCl((IV)-2)((VI)-1)]:

A mixture of [RuHCl(IV-2)(PPh$_3$)] (300 mg, 0.29 mmol) (obtained according to Abdur-Rashid, K. et al. in Organometallics 2001, 20, 1047) and (VI)-1 (70 mg, 0.30 mmol) in toluene (5 ml) was refluxed for 6 hours. The resulting solution was concentrated to 1 ml and hexanes (10 ml) added, resulting in a bright yellow product Yield=261 mg, 90%.

$^1$H NMR (C$_6$D$_6$): −17.75 ppm (dt, $^2$J$_{HP}$=20.6, 25.6 Hz, 1H, RuH), 0.95-3.68 ppm (m, 6H), 6.22-8.83 ppm (m, 42H); $^{31}$P{$^1$H} (C$_6$D$_6$): 38.1 ppm (dd, $^2$J$_{PP}$=292, 32.5 Hz), 40.6 ppm (dd, $^2$J$_{PP}$=292, 31.4 Hz), 67.5 ppm (dd, $^2$H$_{PP}$=32.5, 31.4 Hz) IR (Nujol): 1986 cm$^{-1}$ (vRuH); 3329, 3259 cm$^{-1}$ (vNH).

i) Preparation of the Complex [RuHCl((IV)-2)((VI-2)]:

This complex was prepared using a similar procedure to that described in h). Yield=272 mg, 93%.

$^1$H NMR (C6D$_6$): −17.36 ppm (ddd, $^2$J$_{HP}$=21.7, 21.0, 20.1 Hz, 1H, RuH), 0.85-3.00 ppm (m, 8H), 6.22-6.88 ppm (m, 42H); $^{31}$P {$^1$H} NMR (C$_6$D$_6$): 29.43 ppm (dd, $^2$J$_{PP}$=294, 31.2 Hz), 32.9 ppm (dd, $^2$J$_{PP}$=294, 32.4 Hz), 63.4 ppm (dd, $^2$J$_{PP}$=31.2, 32.4 Hz). IR (Nujol): 2006 cm$^{-1}$ (vRuH), 3320, 3250 cm$^{-1}$ (vNH).

j) Preparation of the Complex [RuHCl((IV)-1)((VI)-1)]:

Synthesis of the precursor [RuHCl((IV)-1)(PPh$_3$)]: THF (20 mL) was added to a mixture of (IV)-1 (2.0 g, 3.6 mmol) and RuHCl(PPh$_3$)$_3$ (3.3 g, 3.4 mmol) and the resulting suspension was refluxed for 6 h under Ar. The solution was then evaporated to dryness under vacuum and the residue was extracted with CH$_2$Cl$_2$ (2×15 ml) and filtered The filtrate was evaporated to dryness and ether (20 ml) was added to the residue. The suspension was stirred for one hour under N$_2$. The red-brown solids were filtered, washed with ether (2×5 ml) and dried under vacuum. Yield=2.46 g, 72%.

$^1$H NMR (C$_6$D$_6$): 6.9-8.0 ppm (m, 35H, PC$_6$H$_5$), 4.56, 4.41, 3.94, 3.78 (br, each 2H, PC$_5$H$_4$), —19.52 (dt, $^2$J$_{HP}$=19.2, $^2$J$_{HP}$=30.6 Hz, RuH). $^1$P{$^1$H} NMR (C$_6$D$_6$): 44.79 ppm (t, $^2$J$_{PP}$=131 Hz, PPh$_3$), 68.25 (br, 2 PC$_5$H$_4$).

Synthesis of the title complex: A solution of (VI)-1 (240 mg, 1.03 mmol) in ThF (5 ml) was added to [RuHCl((IV)-1)(PPh$_3$)] (950 mg, 1.0 mmol) and the resulting solution stirred for two hours at 20° C. The solvent was removed under vacuum and the solids extracted with THF (3.0 ml) and filtered. Hexane (20 ml) was added to the filtrate, yielding a pale yellow solid, which was filtered, washed with hexane (2×5 ml) and dried under vacuum. Yield=623 mg, 67%.

This exists as two diastereomers in the ratio 2:1:

$^1$H NMR (C$_6$D$_6$): −17.91 ppm (dt, $^2$J$_{HP}$=20.2, 26.0 Hz, 1H, RuH of both diastereomers), 1.6-3.4 (several m, 6H dppea), 3.70, 3.75, 3.85, 3.90, 4.09, 4.21, 4.31, 4.60, 5.30 (several m, 8H, PC$_5$H$_4$), 6.6-8.6 (several m, 30H);

Diastereomer 1:

$^{31}$P {$^1$H} NMR (C$_6$D$_6$): 58.4 ppm (dd of AMN, $^2$J$_{PP}$=31 (AM), 35 (AN) Hz), 52.4 (dd of AMN, $^2$J$_{PP}$=286 (MN), 31 (AM) Hz), 47.7 (dd of AMN, $^2$J$_{PP}$=286 (MN), 35 (AN) Hz).

Diastereomer 2:

$^{31}$P {$^1$H} NMR (C$_6$D$_6$): 36.8 ppm (dd of AMN, $^2$J$_{PP}$=32 (AM), 30 (AN) Hz), 33.0 (dd of AMN, $^2$J$_{PP}$=333 (MN), 32.3 (AM) Hz), 27.4 (dd of AMN, $^2$J$_{PP}$=333 (M, 30.5 (AN) Hz).

k) Preparation of the Complex RuHCl((IV-3)((V)-1):

Synthesis of the precursor [RuHCl((IV)-3)(PPh$_3$)], n=1, 2: THF (20 ml) was added to a mixture of (IV)-3 (1.29 g, 2.6 mmol) and RuHCl(PPh$_3$)$_3$ (2.36 g, 2.6 mmol) and the suspension refluxed for 6 h under Ar. The solvent was removed under vacuum and the solids extracted with THF (10 ml) and filtered. The filtrate was evaporated to dryness and a mixture of ether/hexane (1:5) (20 mL) was added. The suspension was stirred vigorously for 2 h. The red-brown solids were filtered off, washed with hexane and dried under vacuum. Yield=1.85 g, 69% (based on a 1:1 mixture of isomers with n=1 and n=2).

Isomer with n=1.

$^1$H NMR (C$_6$D$_6$): −16.72 ppm (dt, $^2$J$_{HP}$=22, 23H=31 Hz, RuH). $^{31}$P{$^1$H} NMR (C$_6$D$_6$): 81 ppm (br, P$_A$ of AMX), 48 (br m, P$_M$ of AMX, $^2$J$_{Hz)}$, 35 (br m, P$_X$ of AMX, $^2$J$_{PP}$=242).

Isomer with n=2.

$^1$H NMR (C$_6$D$_6$): −17.96 (tt, $^2$J$_{HP}$=13.4, $^2$J$_{HP}$=28.5 Hz, RuH). $^{31}$P{$^1$H} NMR (C$_6$D$_6$): 22.8 ppm (t, $^2$J$_{PP}$=40.2 Hz), 4.0 ppm (t, $^2$J Synthesis of the title complex: A solution of (VI)-1 (240 mg, 1.03 mmol) in THF (2.0 ml) was added to 900 mg of [RuHCl((IV)-3)(PPh$_3$)$_n$] (n=1, 2 in 1:1 ratio) and the mixture was stirred for one hour at 20° C. under N$_2$. The mixture was filtered and hexanes (20 ml) were added to the filtrate, precipitating a yellow-green solid which was filtered, washed with hexane and dried under vacuum. Yield=582 mg, 76%.

This exists as two diastereomers in a ratio 1.5:1:

Diastereomer 1:
$^1$H NMR ($C_6D_6$): −18.1 ppm (dt, $^2J_{HP}$=19.8, 24.8 Hz, 1H, RuH); $^{31}$P {$^1$H} NMR ($C_6D_6$): 53.3 ppm (dd, $^2J_{PP}$=28, 280 Hz), 46.3 (dd, $^2J_{PP}$=28, 31 Hz), 31.4 (dd, $^2J_{PP}$=280, 31 Hz).

Diastereomer 2:
$^1$HNMR ($C_6D_6$): −18.2 (dt, $^2J_{HP}$=19.8, 24.6 Hz, 1H, RuH); $^{31}$P {$^1$H} NMR ($C_6D_6$): 54.4 ppm (dd, $^2J_{PP}$=36, 283 Hz), 46.3 (dd, $^2J_{PP}$=36, 35 Hz), 37.4 (dd, $^2J_{PP}$=283, 35 Hz).

l) Preparation of the Complex Trans-[RuH$_2$((IV)-2)((VI)-1)]:

Synthesis of precursor [K(18-crown-6)][RuH$_3$((IP)-2)(PPh$_3$)]: THF (2 ml) was added to a mixture of [RuHCl((IV)-2)(PPh$_3$)] (100 mg, 0.10 mmol), KH (20 mg, 0.5 mmol) and 18-crown-6 (26 mg, 0.10 mmol) under an atmosphere of H$_2$ gas. The mixture was stirred for 5 hours, filtered under a nitrogen atmosphere and hexane (10 ml) added to the filtrate, precipitating a pale red-brown solid. Yield=95 mg, 74%.

$^1$H NMR ($C_6D_6$): −9.98 ppm (m, 1H, RuH), −9.36 ppm (m, 1H, RuH), −8.97 ppm (m, 1H, RuH), 3.24 ppm (s, 24H, CH$_2$), 6.24-8.76 ppm (m, 47H). $^{31}$P {$^1$H} NMR ($C_6D_6$): 59.1 ppm (m), 61.2 ppm (m), 64.7 ppm (m). IR (Nujol): 1799, 1836 cm$^{-1}$ (vRuH).

Synthesis of the title complex: A mixture of [K(8-crown-6)] [RuH$_3$((IV)-2)(PPh$_3$)] (100 mg, 77 mmol) and (VI)-1 (20 mg, 86 mmol) in C$_6$D$_6$ (0.6 ml) was allowed to stand for 12 hours. The NMR spectrum shows a clean formation of the trans-dihydride complex.

$^1$H NMR ($C_6D_6$) Hydride region: −5.16 (m) ppm (m), −6.49 (m). $^{31}$P {$^1$H} NMR ($C_6D_6$): 67.4 (dd, $^2J_{PP}$=280, 33.4 Hz, 72.8 (dd, $^2J_{PP}$=280, 38.6 Hz, 81.6 (dd, $^2J_{PP}$=38.6, 33.4 Hz m) Preparation of the Complex [Ru(AcO)$_2$((VI)-1)$_2$]:

A solution of Ru$_2$(AcO)$_4$ (13.1 mg, 0.03 mmol) (prepared according to Lindsay et al. in *J.Chem.Soc.Dalton Trans.* 1985, 2321) and (VI)-1 (27.5 mg, 0.12 mmol) in CH$_2$Cl$_2$ (3 ml) was left for 24 h at ambient temperature. Removal of the solvent in vacuum gave 38 mg of a bright yellow powder. Yield=93%.

$^{31}$P{$^1$H} NMR (CD$_2$Cl$_2$): 50.2(s), 64.8 ppm (s).

EXAMPLE 2

Catalytic Hydrogenation of Ketones Using [RuXY((VI)$_2$] or [RuXY(VI)(IV)]

Under an atmosphere of hydrogen gas (1-3 atm) at room temperature, catalytic amounts of the complexes with a ligand of formula (VI) described in Example 1, together with 3-10 equivalents of KO$^i$Pr effectively and readily catalyzed the hydrogenation of the neat ketone to the corresponding alcohol. A typical catalytic run using [RuHCl((VI)-2)$_2$] and acetophenone as substrate is as follows:

Acetophenone (2.0 g) was added under a flow of hydrogen gas to a Schlenk flask containing [RuHCl((VI)-2)$_2$] (5 mg) and KO$^i$Pr (5 mg). The flask was cooled to liquid nitrogen temperature, filled with H$_2$ gas, closed and allowed to gradually warm to room temperature. The mixture was vigorously stirred for 12 hours. A $^1$H NMR spectrum of the reaction mixture indicated complete conversion of the ketone to the alcohol. Under these conditions, the complexes reported in Table 2 resulted in 100% conversion of the ketone to the corresponding alcohol (Table 2).

TABLE 2

Hydrogenation of ketones using some [RuXY((VI))$_2$] or [RuXY(VI)(IV)]

| Test | Sub. | Complex | Com/base | Conv. |
|---|---|---|---|---|
| 1 | 1 | [RuHCl((VI)-1))$_2$] | 500/5000 | 100 |
| 1 | 1 | [RuHCl((VI)-1))$_2$] | 500/2500 | 100 |
| 2 | 1 | [RuHCl((VI)-2)$_2$] | 500/2500 | 100 |
| 3 | 1 | [RuHCl((VI)-3)$_2$] | 400/2000 | 100 |
| 4 | 1 | [RuCl$_2$((VI)-1))$_2$] | 400/2000 | 100 |
| 5 | 1 | [RuCl$_2$((VI)-2)$_2$] | 400/2000 | 100 |
| 6 | 1 | [RuCl$_2$((VI)-3)$_2$] | 370/1900 | 100 |
| 7[1)] | 1 | [Ru(AcO)$_2$((VI)-1))$_2$] | 100/500 | 100 |
| 8 | 2 | [RuCl$_2$((VI)-1))$_2$] | 240/1200 | 100 |
| 9 | 2 | [RuCl$_2$((VI)-2)$_2$] | 240/1200 | 100 |
| 10 | 2 | [RuHCl((VI)-1))$_2$] | 240/1200 | 100 |
| 11 | 2 | [RuHCl((VI)-3))$_2$] | 190/1200 | 100 |
| 12 | 3 | [RuCl$_2$((VI)-1))$_2$]* | 2500/12500 | 100 |
| 13 | 3 | [RuCl$_2$((VI)-2)$_2$]* | 2500/12500 | 100 |
| 14 | 3 | [RuHCl((VI)-1))$_2$]* | 2500/12500 | 100 |
| 15 | 3 | [RuHCl((VI)-2)$_2$]* | 2500/12500 | 100 |
| 16 | 4 | [RuCl$_2$((VI)-1)$_2$] | 400/2000 | 100 |
| 17 | 4 | [RuHCl((VI)-1)$_2$] | 400/2000 | 100 |
| 18 | 4 | [RuHCl((VI)-2)$_2$] | 1600/800 | 100 |
| 19 | 5 | [RuHCl((VI)-1))$_2$] | 400/2000 | 100 |
| 20 | 1 | [RuHCl((IV)-2)((VI)-1))] | 240/1200 | 100[2a)] |
| 21 | 1 | [RuHCl((IV)-2)((VI)-2))] | 240/1200 | 100[2b)] |
| 22 | 1 | [RuHCl((IV)-3)((VI)-1))] | 240/1200 | 100 |
| 23 | 2 | [RuHCl((IV)-2)((VI)-1))] | 300/1500 | 100 |
| 24 | 2 | [RuHCl((IV)-2)((VI)-2))] | 300/1500 | 100 |
| 25 | 3 | [RuHCl((IV)-1)((VI)-1))] | 1750/8500 | 100 |
| 26 | 3 | [RuHCl((IV)-3)((VI)-1))] | 1850/8500 | 100 |
| 27 | 4 | [RuHCl((IV)-1)((VI)-1))] | 550/2700 | 100 |
| 28 | 4 | [RuHCl((IV)-3)((VI)-1))] | 580/2900 | 100 |
| 29 | 5 | [RuHCl((IV)-1)((VI)-1))] | 500/2500 | 100 |
| 30 | 5 | [RuHCl((IV)-3)((VI)-1))] | 560/2800 | 100 |

Sub.: Substrate: 1) = acetophenone, 2) = acetone, 3) = 2,2-dimethyl-1-phenyl-propanone, 4) = 3,3-dimethyl-2-butanone, 5) = 5-hexen-2-one
Com/base: molar ratio in ppm relative to the substrate
Conv. = conversion (in %, analysed by GC or NMR) of the ketone into the corresponding alcohol (namely 1-phenyl-1-ethanol, isopropanol, 2,2-dimethyl-1-phenyl-propanol, 3,3-dimethyl-2-butanol and 5-hexen-2-ol respectively) after 12 hours.
Reaction conditions: H$_2$ gas (≈3.5 atm.), 20° C.
*Hydrogenation performed in 1 g of C$_6$D$_6$ for 2.5 g of substrate
[1)]test performed at 40° C. and under H$_2$ gas (≈60 atm.), according the hydrogenation conditions described in example 3.
[2a)]e.e. (S enantiomer) = 10%;
[2b)]e.e. (S enantiomer) = 40%

EXAMPLE 3

Catalytic Hydrogenation of 2-ethyl-4-(2',2',3'-trimethyl-3'-cyclopenten-1'-yl)-2-buten-1-al Using [RuXY((VI)-1)$_2$] or [RuXY((VI)-1)(IV)-4)] Prepared in situ Preparation In Situ of a Ru/(VI)-1 Solution from [Ru(COD)(Methylallyl)$_2$]:

The entire procedure described herein below is carried out under inert atmosphere. 31.9 mg (0.1 mmol) of [Ru(COD)(methylallyl)$_2$] were dissolved in 1 ml of CH$_2$Cl$_2$, and 0.10 mmol of HBF$_4$.Et$_2$O were added to the solution. The solution thus obtained was stirred at room temperature for 2 h, then 45.8 mg (0.2 mmol) of 2-diphenylphosphino ethylamine ((VI)-1) were added and the resulting mixture stirred for 2 h at room temperature.

Preparation In Situ of a Ru/(VI)-1 Solution from [Ru(C$_6$H$_6$)(Cl)$_2$]$_2$:

A solution of [RuCl$_2$(C$_6$H$_6$)]$_2$ (25.0 mg, 0.05 mmol) and (VI)-1 (45.8 mg, 0.20 mmol) in DMF (1.5 ml) was heated to 100° C. for 1 h. The solvent was stripped off in vacuum from the yellow solution, and the residue (yellow solid) taken up in $CH_2Cl_2$ (0.5 ml).

Hydrogenation:

1.0 µL of one of the above mentioned Ru/(VI)-1 solutions (0.0001 mmol, 10 ppm with respect to the substrate) was added to a solution of the substrate (2.06 g, 10.0 mmol) and t-BuOK (100.8 mg, 0.90 mmol) in i-PrOH (2.20 ml), and the resulting solution exposed to $H_2$ (40 bar) at 60° with magnetic stirring. The molar proportions correspond to 1 mol of precatalyst per 9000 mol of t-BuOK per 100'000 mol of substrate, {1:9000:100'000}, and the initial concentration of substrate in the i-PrOH was ~2.4 M. Conversion to 2-ethyl-4-(2',2',3'-trimethyl-3'-cyclopenten-1'-yl)-2-buten-1-ol was complete within 3 h. Further runs were done on the same scale and under the same conditions, but with varying amounts of complex and t-BuOK, and essentially the same results were obtained except for the conversion at very low complex loading. The latter runs, at 1-5 ppm catalyst, relative to the amount of substrate, can be pushed to completion by prolonging the reaction time and/or raising the pressure and/or the temperature. A run with a Ru/(VI)-1/(IV)-1 solution generated in situ has been also performed.

TABLE 3

Hydrogenation of a sandranal using some [RuXY((VI))$_2$] or [RuXY(VI)(IV)]

| Test | Complex | Com/base | Conv./time | Conv./time |
|---|---|---|---|---|
| 1 | [RuXY((VI)-1))$_2$]$^{a)*}$ | 100/90000 | 100/3 h | |
| 2 | [RuXY((VI)-1))$_2$]$^{a)*}$ | 5/90000 | 94/3 h | 100/20 h |
| 3 | [RuXY((VI)-1))$_2$]$^{a)*}$ | 2/90000 | 34/3 h | 88/20 h |
| 4 | [RuXY((VI)-1))$_2$]$^{a)*}$ | 1/90000 | 28/3 h | 79/20 h |
| 5 | [RuCl$_2$((VI)-1)$_2$]*** | 100/45000 | 100/1.5 h | |
| 6 | [RuCl$_2$((VI)-1)$_2$]*** | 10/4500 | 50/3 h | 100/20 h |
| 7 | [RuCl$_2$((VI)-1)$_2$]*** | 10/45000 | 100/1.5 h | |
| 8 | [RuXY((VI)-1)((IV)-4)$^§$]$^{a)**}$ | 10/45000 | 100/5 h | |
| 9 | [RuHCl((VI)-1))$_2$]$^{b)}$ | 10/500 | 97/3 h | |

Sandranal: 2-ethyl-4-(2',2',3'-trimethyl-3'-cyclopenten-1'-yl)-2-buten-1-al
$^{a)}$X and Y represent a hydrogen atom or an alkoxy radical
$^{b)}$For comparison, test performed with a complex pre-formed according to the procedure of example 1b)
Com/base: molar ratio in ppm relative to the substrate
Conv./time = conversion (in %, analyzed by GC) of sandranal into the corresponding alcohol at the indicated time in hours.
§: structure of the ligand (IV)-4: Ph$_2$P∼∼∼PPh$_2$
Ligand (IV)-4 is commercially available from FLUKA.
*complex prepared in situ from [Ru(COD)(methylallyl)$_2$]
**complex prepared in situ from [Ru(COD)(methylallyl)$_2$], according to the procedure here-in-above, except that it has been added 0.1 mmol of (VI)-1 and 0.1 mmol (IV)-4
***complex prepared from [Ru(C$_6$H$_5$)(Cl)$_2$]$_2$.

EXAMPLE 4

Catalytic Hydrogenation of Some Ketones Using [RuCl$_2$(VI)-1)$_2$]Prepared In Situ Using a hydrogenation procedure similar to the one described in example 3. The results are listed in table 4.

TABLE 4

Hydrogenation of a some ketones using [RuCl$_2$((VI)-1)$_2$]

| Test | Sub | Catalyst: | Com/base | Conv. |
|---|---|---|---|---|
| 1 | 1 | [RuCl$_2$((VI)-1)$_2$]* | 10/45000 | 63 |
| 2 | 1 | [RuCl$_2$((VI)-1)$_2$]* | 10/4500 | 15 |
| 3 | 2 | [RuCl$_2$((VI)-1)$_2$]* | 10/45000 | 99 |
| 4 | 2 | [RuCl$_2$((VI)-1)$_2$]* | 10/4500 | 99 |

Sub: Substrate: 1) 3,3-dimethyl-5-(2',2',3'-trimethyl-3'-cyclopenten-1'-yl)-4-penten-2-one; 2) = 4-(2',6',6'-trimethyl-1'-cyclohexen-1'-yl)-3-buten-2-one
Com/base: molar ratio in ppm relative to the substrate
Conv. = conversion (in %, analyzed by GC) of the ketone into the corresponding alcohol after 3 hours.
*complex prepared from the [Ru(C$_6$H$_5$)(Cl)$_2$]$_2$ as in example 3.

EXAMPLE 5

Catalytic Hydrogenation of Imines Using [RuXY((VI))$_2$] or [RuXY(VI)(IV)]

Under an atmosphere of hydrogen gas (1-3 atm) at room temperature, catalytic amounts of the complexes with a ligand of formula (VI) described in Example 1, together with 5-10 equivalents of KO$^i$Pr effectively and readily catalyzed the hydrogenation of the imine to the corresponding amine. A typical catalytic run using [RuHCl((VI)-1)$_2$] and N-(1-phenylethylidene)-benzenamine as substrate is as follows:

N-(1-phenylethylidene)-benzenamine (4.0 g) and C$_6$D$_6$ (1 g) were added under a flow of hydrogen gas to a Schlenk flask containing [RuHCl((VI)-1)$_2$] (105 mg) and KO$^i$Pr (10 mg). The flask was cooled to liquid nitrogen temperature, filled with H$_2$ gas, closed and allowed to gradually warm to room temperature. The mixture was vigorously stirred for 12 hours. A $^1$H NMR spectrum of the reaction mixture indicated complete conversion of the imine to the amine. Under these conditions, the complexes reported in Table 5 resulted in 100% conversion of the imine to the corresponding amine (Table 5).

TABLE 5

Hydrogenation of imines using some [RuXY((VI))$_2$] or [RuXY(VI)(IV)]

| Test | Sub. | Complex | Com/base | Conv./time |
|---|---|---|---|---|
| 1 | 1 | [RuCl$_2$((VI)-1))$_2$] | 240/1200 | 100/<12 h |
| 2 | 1 | [RuCl$_2$((VI)-2))$_2$] | 2700/13500 | 100/<4 h |
| 3 | 1 | [RuHCl((VI)-1))$_2$] | 2700/13500 | 100/<4 h |
| 4 | 1 | [RuHCl((VI)-2)$_2$] | 2700/13500 | 100/<4 h |
| 5 | 1 | [RuHCl((IV)-2)((VI)-1))] | 1700/8500 | 100/12 h |
| 6 | 1 | [RuHCl((IV)-2)((VI)-2))] | 1700/8500 | 100/12 h |
| 7 | 1 | [RuHCl((IV)-1)((VI)-1))] | 1000/5000 | 100/12 h |
| 8 | 1 | [RuHCl((IV)-3)((VI)-1))] | 1000/5000 | 100/12 h |
| 9 | 2 | [RuCl$_2$((VI)-1))$_2$] | 1000/5000 | 100/<8 h |
| 10 | 2 | [RuCl$_2$((VI)-2))$_2$] | 480/2400 | 100/<12 h |
| 11 | 2 | [RuCl$_2$((VI)-3))$_2$] | 1100/5500 | 100/<24 h |
| 12 | 2 | [RuHCl((VI)-1))$_2$] | 380/1900 | 100/<12 h |
| 13 | 2 | [RuHCl((VI)-2))$_2$] | 500/2500 | 100/<12 h |
| 14 | 2 | [RuHCl((IV)-2)((VI)-1))] | 1000/5000 | 100/12 h |
| 15 | 3 | [RuCl$_2$((VI)-1))$_2$]* | 550/2750 | 100/<12 h |
| 16 | 3 | [RuCl$_2$((VI)-2))$_2$]* | 550/2750 | 100/<12 h |
| 17 | 3 | [RuHCl((VI)-1))$_2$]* | 550/2750 | 100/<12 h |
| 18 | 3 | [RuHCl((VI)-2))$_2$]* | 550/2750 | 100/<12 h |
| 19 | 3 | [RuHCl((IV)-2)((VI)-1))]* | 1000/5000 | 100/12 h |

Sub.: Substrate: 1) = N-(phenylmethylene)-benzenamine, 2) = N-(1-phenylethylidene)-benzenamine, 3) = N-(1-phenylethylidene)-benzenemethanamine
Com/base: molar ratio in ppm relative to the substrate
Conv./time = conversion (in %, analysed by NMR) of the imine into the corresponding amine at the indicated time in hours.
Reaction conditions: H$_2$ gas (≈3.5 atm.), 20° C.
*Hydrogenation of the neat substrate

EXAMPLE 6

Catalytic Hydrogenation of an Aldehyde Using [Ru(V)$_2$XY] or [Ru(VI)$_2$XY] Prepared In Situ i) Preparation of the New Ligands of Formula (V) or (VI) Used in the Example A. 3-(Dicyclohexylphosphino)-1-propylamine ((VI)-4)

10 g (54 mmol) dicyclohexylphosphine, 3.1 g (54 mmol) allylamine and 0.2 g ditertiobutylperoxide were stirred under nitrogen in an autoclave for 2 hours at 150° C. The resulting mixture was fractionnated by vacuum distillation to give the desired aminophosphine (colorless liquid) in 92% purity and 50% yield.

$^3$C-NMR (CDCl$_3$): 43.6(t, CH$_2$—NH$_2$); 33.4-33.3(d, P—CH cyclohexyl); 33.4-18.3(t, cyclohexyl) MS (relative intensities): 255(M+, 0.6), 172(100), 130(54.7), 131(39.8), 90(35.1).

B. 2-[2-(Diisobutylphosphino)-ethyl]pyridine ((V)-1)

10 g (68 mmol) diisobutylphosphine, 7.1 g (68 mmol) 2-vinyl pyridine and 0.1 g 2,2'-azobis(isobutyronitrile) (AIBN, VAZO® 64) were stirred under nitrogen in a glass reactor for 2 hours at 85° C. The resulting mixture was fractionated by vacuum distillation to give the desired aminophosphine (colourless liquid) in 95% purity and 60% yield.

$^{13}$C-NMR (CDCl$_3$): 160.4(s, =C—N Py); 149.3-122.9(d, Py ring); 30.3(t, CH$_2$-Py); 28.9(t, P—CH$_2$CH$_2$-Py); 38.5(t, PCH$_2$ iBu) $^{31}$P {$^1$H} NMR (CDCl$_3$): 45.66 ppm. MS (relative intensities): 194(100), 138(47), 136(15.6), 195(13.5).

C. 2-[2-Diisobutylphosphino)-ethyl]-1H-Imidazole ((V)-2)

10 g (68 mmol) diisobutylphosphine, 6.4 g (68 mmol) 1-vinyl imidazole and 0.1 g 2,2'-azobis(isobutyronitrile) (AIBN, VAZO® 64) were stirred under nitrogen in a glass reactor for 2 hours at 85° C. The resulting mixture was fractionated by vacuum distillation to give the desired aminophosphine (colourless liquid) in 96% purity and 50% yield.

$^{13}$C-NMR (CDCl$_3$) 136.7, 129.5, 118.5(d, Im); 44.8(t, C—N Im); 31.2 (t, P—CH$_2$CH$_2$-Im); 38.9(t, PCH$_2$ iBu). MS (relative intensities): 240(M+, 100), 239(89), 128(91), 95(90).

ii) Preparation In Situ of a Ru/(ligand) Solution from [Ru(COD)(methylallyl)$_2$]

The whole procedure described herebelow is carried out under inert atmosphere. 31.9 mg (0.1 mmol) of [Ru(COD)(methylallyl)$_2$] were dissolved in 1 ml of CH$_2$Cl$_2$, and 0.10 mmol of HBF$_4$.Et$_2$O were added to the solution. The solution thus obtained was stirred at room temperature for 2 h, then 0.2 mmol of the desired ligand were added and the resulting mixture stirred for 2 h at room temperature. Finally, to the resulting solution were added 9 ml of CH$_2$Cl$_2$.

iii) Hydrogenation

In a Schlenk tube, in a glove box under inert atmosphere, an appropriate quantity of sodium methoxide, according to Table 6 or 7 (column A), was dissolved in an appropriate quantity of iso-propanol, according to Table 6 or 7 (column B). Then an appropriate quantity of Sandranal, according to Table 6 or 7 (column B), was added and the mixture was stirred for 5 minutes. To the resulting solution was added an appropriate volume of the Ru/(ligand) solution, according to Table 6 or 7 (column C), the latter being obtained as in here-in-above using the desired ligand. After 10 minutes sting the solution was transferred into a bomb wherein solution was warmed at 40° C. and left under 30 atm. of H$_2$. The reaction was followed by GC, and once the starting product has disappeared the reaction was cooled to room temperature and the pressure lowered to 1 atm.

The ligand structure, the quantities and results for each test is summarized in Table 6 or 7.

TABLE 6

Hydrogenation of Sandranal using a Ru complex with ligands of formula (V)

| Test | Complex | A | B | C | Com/base | Conv./Time |
|---|---|---|---|---|---|---|
| 1 | [RuXY((V)-1))$_2$]$^{a)}$ | 0.3 | 25.75 | 1 | 80/44000 | 86/16 h |
| 2 | [RuXY((V)-2))$_2$]$^{a)}$ | 0.3 | 25.75 | 1 | 80/44000 | 64/16 h |

TABLE 7

Hydrogenation of Sandranal using a Ru complex with ligands of formula (VI)

| Test | Complex | A | B | C | Com/base | Conv./time |
|---|---|---|---|---|---|---|
| 1 | [RuXY((VI)-4))$_2$]$^{a)}$ | 0.3 | 25.75 | 1 | 80/44000 | 74/8 h |
| 2 | [RuXY((VI)-4))$_2$]$^{a)}$ | 0.3 | 25.75 | 0.5 | 40/44000 | 78/20 h |
| 3 | [RuXY((VI)-4))$_2$]$^{a)}$ | 0.3 | 25.75 | 0.25 | 20/44000 | 80/24 h |
| 4 | [RuXY((VI)-1))$_2$]$^{a)}$ | 0.6 | 103 | 0.5 | 10/22000 | 95/6 h |
| 5* | [RuXY((VI)-5))$_2$]$^{a)}$ | 1.2 | 103 | 0.5 | 10/45000 | 91/7 h |

$^{a)}$X and Y represent a hydrogen atom or an alkoxy radical
Sandranal: 2-ethyl-4-(2',2',3'-trimethyl-3'-cyclopenten-1'-yl)-2-buten-1-al
Com/base: molar ratio in ppm relative to the substrate
Conv./time = conversion (in %, analyzed by GC) of the aldehyde into the corresponding alcohol at the indicated time in hours.

*ligand (VI-5): Ph$_2$P~~~NH$_2$ (from FLUKA)
A = grams of NaOMe used in the test
B = grams of $^i$PrOH used in the test; grams of Sandranal used in the test
C = volume (in ml) of the Ru/(V) or Ru/(VI) solution used in the test

EXAMPLE 7

Catalytic hydrogenation of ketones using [RuXY((V'))$_2$]

TABLE 8

Structure of the ligands of formula (V') used for the synthesis of the corresponding complexes

| structure | name |
|---|---|
| [oxazoline-phenyl-PPh$_2$ with isopropyl] | (V')-1 |
| [isoquinoline-naphthyl-phenyl-PPh$_2$] | (V')-2 |

TABLE 8-continued

Structure of the ligands of formula (V') used for the synthesis of the corresponding complexes

| structure | name |
|---|---|
| [structure with PPh₂, benzene ring, N=CH, isobutyl group] | (V')-3 |
| [structure with PPh₂, benzene ring, N=CH, bicyclic pinane-type group] | (V')-4 |

Ligands (V')-1 and (V')-2 are commercially available from STREM. Ligands (V')-3 and (V')-4 were obtained from the corresponding amine according the method described by Gao et al. in Polyhedron 1996, 15, 1241

Preparation of the complex [RuCl$_2$((V)-4)$_2$]:

This complex has been obtained by reacting (V')-1 (562 mg, 1.408 mmole) and [RuCl$_2$(DMSO)$_4$] (341 mg, 0.616 mmole) in refluxing toluene (20 ml) under stirring for 8 hour, during which an orange precipitate is formed. After cooling at room temperature, the solid was filtered washed with cold toluene and then with hexane and finally dried under vacuum. 376 mg of [RuCl$_2$((V')-1)$_2$] were obtained (yield 66%).

$^{31}$P{H} NMR (CD$_2$Cl$_2$): 60.7 ppm (s).

Preparation of the Complex [RuCl$_2$((V')-2)$_2$]:

This complex has been obtained by reacting (V')-2 (255 mg, 0.580 mmole) and [RuCl$_2$(PPh$_3$)$_3$] (270 mg, 0.282 mmole) in toluene (20 ml) during 30 min at room temperature. Then the solution was refluxed for 8 hour and next the resulting red-purple solution cooled at room temperature. After a small amount of solid was removed by filtration, then the resulting solution was concentrated to 5 ml and the product precipitated by adding 100 ml of pentane and the suspension stirred for 2 hours. Finally, the precipitate was collected by filtration, washed with pentane and dried under vacuum. 300 mg of [RuCl$_2$((V')-2)$_2$] were obtained (yield=100%)

$^1$H NMR (CD$_2$Cl$_2$): Aromatic protons between 6.2 and 9.2 ppm. $^{31}$P {H} NMR (CD$_2$Cl$_2$): 49.6 ppm (s).

Preparation of the Complex [RuCl$_2$((V)-3)$_2$]:

This complex has been obtained by reacting (V')-3 (190 mg, 0.529 mmole) and [RuCl$_2$(PPh$_3$)$_3$] (221 mg, 0.231 mmole) in CH$_2$Cl$_2$ (10 mL) for 18 hours at room temperature. The resulting red solution was concentrated to 1 ml and the product was precipitated by adding 50 ml of pentane and stirring for 2 hours. Finally, the precipitate was collected by filtration, washed with pentane and dried under vacuum. 160 mg of red orange [RuCl$_2$((V')-3)$_2$] were obtained (yield=78%)

$^{13}$C NMR (CD$_2$Cl$_2$): N—CH$_2$ at 66.7 ppm; N—CH$_2$—CH$_2$ at 41.5 ppm; CH(CH$_3$)$_2$ at 28.8 ppm; CH$_3$ at 22.5 and 23.1 ppm; N=CH at 168.8 ppm, aromatic protons between 127 and 140 ppm. $^{31}$P {$^1$H} NMR (CD$_2$Cl$_2$): 52.6 ppm (s).

Preparation of the Complex [RuCl$_2$((V')$_4$)$_2$]:

This complex has been obtained by reacting (V')$_4$ (225 mg, 0.529 mmole) and [RuCl$_2$(PPh$_3$)$_3$] (230 mg, 0.240 mmole) in CH$_2$Cl$_2$ (10 ml) for 3 days at room temperature. The resulting solution was concentrated to 1 ml, the product was precipitated by adding 50 ml of pentane and the suspention stirred for 2 hours. Finally, the precipitate was collected by filtration, washed with pentane and dried under vacuum. 140 mg of [RuCl$_2$((V')-3)$_2$] were obtained (yield=60%)

$^1$H NMR (CD$_2$Cl$_2$): Aliphatics protons between e 0.6 and 5.2 ppm, Aromatic protons between 6.2 and 7.5 ppm, N=CH at 8.15 ppm (AB system). $^3$C NMR (CD$_2$Cl$_2$): Aliphatic carbons between 14 and 76 ppm (20 signals, all of the carbons give two resonances), Aromatic protons between 127 and 140 ppm, N=CH at 168.2 and 169.1 ppm. $^{31}$P {$^1$H} NMR (CD$_2$Cl$_2$): 52.7 ppm (AB system).

Hydrogenation a Substrate to the Corresponding Alcohol

An aliquot of a 2.1 M solution of substrate in $^i$PrOH, representing 20 mmoles of said substrate, the desired amount of $^t$BuOK were introduced into an autoclave and stirred until complete dissolution of the base. Afterward, to said solution was added an adequate amount of a stock solution of the desired complex dissolved in CH$_2$Cl$_2$ (typical metal concentration is 0.02 M). Then, the autoclave was purged 3 times with H$_2$, and finally warmed at 60° C. under 45 bar of H$_2$. The reaction was followed by GC, and once the starting product has disappeared the reaction mixture was cooled to room temperature and the pressure lowered to 1 atm. The results are summarized in the Table 9.

TABLE 9

Hydrogenation of a substrate using some complexes [RuXY((V'))$_2$]

| Test | Sub. | Complex | Com/base | Conv./time |
|---|---|---|---|---|
| 1 | 1 | [RuCl$_2$((V')-1)$_2$] | 10/4500 | 12/24 h |
| 2 | 1 | [RuCl$_2$((V')-1)$_2$] | 10/45000 | 27/24 h |
| 3 | 1 | [RuCl$_2$((V')-2)$_2$] | 10/4500 | 9/24 h |
| 4 | 1 | [RuCl$_2$((V')-2)$_2$] | 10/45000 | 28/24 h |
| 5 | 2 | [RuCl$_2$((V')-2)$_2$] | 100/45000 | 7/24 h |
| 6 | 2 | [RuCl$_2$((V')-2)$_2$] | 100/450000 | 21/24 h |
| 7 | 1 | [RuCl$_2$((V')-3)$_2$] | 10/4500 | 45/24 h |
| 8 | 1 | [RuCl$_2$((V')-3)$_2$] | 10/45000 | 100/6 h |
| 9 | 1 | [RuCl$_2$((V')-4)$_2$] | 10/4500 | 68/24 h |
| 10 | 1 | [RuCl$_2$((V')-4)$_2$] | 10/45000 | 100/24 h |

Sub. = substrate, 1) = acetophenone, 2) = 3,3-dimethyl-5-(2',2',3'-trimethyl-3'-cyclopenten-1'-yl)-4-penten-2-one.
Com/base: molar ratio in ppm relative to the substrate
Conv./time = conversion (in %, analyzed by GC) of the substrate into the corresponding alcohol at the indicated time in hours

EXAMPLE 8

Catalytic Hydrogenation of Acetophenone using Some [RuXY((VI)-1)$_2$] Without Addition of a Base Under an atmosphere of hydrogen gas (40 atm) at 60° C., catalytic amounts of [RuHCl((VI)-1)$_2$] described in Example 1, readily catalyzed the hydrogenation of acetophenone to phenylethanol without the addition of a base. A typical catalytic run for a catalyst/substrate (c/s) ratio of 10 ppm and using [RuHCl((VI)-1)$_2$] is as follows: In a Schlenk flask, under Ar and at ambient temperature, [RuHCl((VI)-1)$_2$] (12 mg, 0.02 mmol), (as obtained in example 1b), was suspended in i-PrOH (1 ml) and the resulting suspension stirred for ca. 5 min. 20 μl (0.0004 mmol) of the finely dispersed light-yellow suspension of [RuHCl((VI)-1)$_2$] were added to a solution of acetophenone (4.80 g, 40 mmol) in i-PrOH (14.4 ml) that had been charged into a autoclave under Ar. The autoclave was sealed and pressurised with 40 bar of H₂, and its contents stirred and heated to 60° C. Samples for analysis by GC were periodically withdrawn, and the reaction times and the results are given in the Table 10.

TABLE 10

Hydrogenation of acetophenone using [RuHCl((VI)-1)₂] without base

| Test | Complex | Com | Conv./time | Conv./time |
|------|---------|-----|------------|------------|
| 1 | [RuHCl((VI)-1)₂] | 100 | 100/10 m | |
| 2 | [RuHCl((VI)-1)₂] | 10 | 70/45 m | 100/3 h |
| 3 | [RuHCl((VI)-1)₂] | 2 | 93/4 h | |
| 4 | [RuHCl((VI)-1)₂]* | 100 | 8/20 h | |
| 5 | [Ru(AcO)₂((VI)-1)₂] | 100 | 65/3 h | 100/20 h |
| 6 | [Ru(AcO)₂((VI)-1)₂] | 10 | 100/20 h | |

Com: molar ratio in ppm relative to the substrate
Conv./time = conversion (in %, analyzed by GC) of the substrate into the corresponding alcohol at the indicated time in hours (h) or in minute (m)
*for comparison, test performed with the same experimental procedure but without H₂ gas (reduction by hydrogen transfer)

What is claimed is:

1. A process for the hydrogenation, using molecular hydrogen (H₂), of a C=O double bond of a substrate into the corresponding hydrogenated compound, in the presence of a complex and a base, said process being characterized in that said complex is of formula (II):

$$[Ru(L)_m(L')_wXY] \quad (II)$$

wherein X and Y represent, simultaneously or independently, a hydrogen or halogen atom, a hydroxy radical, or a C1 to C8 alkoxy or acyloxy radical;
m is 1 or 2,
wherein w is 1, m is 1; or
wherein w is 0, m is 2;
L represents a bidentate N-P ligand of general formula

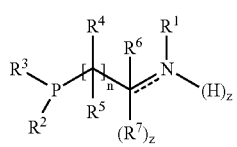
(III)

in which formula (III) the dotted line indicates a single or double bond;
n is an integer from 1 to 4; z is 0 or 1 when the carbon-nitrogen bond with the dotted line represents a double, respectively single bond;
R' represents a hydrogen atom, a linear, branched or cyclic C₁ to C₁₀ alkyl or alkenyl group, possibly substituted, a R*CO acyl group, or a R*SO₂ group, R* representing a C₁ to C₈ alkyl or aryl group;
R² and R³ represent, simultaneously or independently, a linear, branched or cyclic C₁ to C₈ alkyl or alkenyl group, possibly substituted, an aromatic ring, possibly substituted, or an OR²' or NR²'R³'group, R²' and R³' being defined as R² and R³, or said groups R² and R³ being possibly bonded together to form a saturated or aromatic ring having 5 to 10 atoms and including the phosphorous atom to which said R² and R³ groups are bonded;
R⁴, R⁵, R⁶ and R⁷ represent, simultaneously or independently, a hydrogen atom, a linear, branched or cyclic C₁ to C₁₀ alkyl or alkenyl group, possibly substituted, an aromatic ring, possibly substituted, or an OR⁴' or NR⁴'R⁵' group, R⁴' and R⁵' being defined as R⁴ and R⁵ or two distinct R⁴ and/or R⁵ groups being possibly bonded together to form a C₅ to C₈ saturated or aromatic ring including the carbon atoms to which each of said R⁴ or R⁵ group is bonded; and L' represents a bidentate P-P ligand of formula

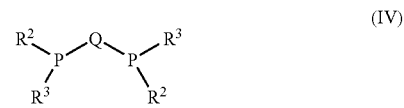
(IV)

wherein R² and R³ are defined as in formula (III), and Q represents a linear or cyclic C₂-C₇ alkylene radical, possibly substituted, a metallocenediyl or a C₆-C₂₂ arylene or biaryldiyl radical, possibly substituted, and
the possible substituents of R¹ to R⁷ and Q are C₁ to C₁₀ alkoxy or polyalkyleneglycol groups, carboxylic esters, C₁ to C₆ alkyl groups, or C₅ to C₁₂ cycloalkyl or aromatic groups;
wherein the substrate reduced is of formula:

(I)

wherein W is an oxygen atom, and R^a and R^b represent simultaneously or independently a hydrogen, an aromatic group possibly substituted, a cyclic, linear or branched alkyl or alkenyl group, possibly substituted, or R^a and R^b form a ring, possibly substituted;
the possible substituents of R^a and R^b are halogen atoms, OR^c, NR^c₂ or R^c groups, in which R^c is a hydrogen atom or a C₁ to C₁₀ cyclic, linear or branched alkyl or alkenyl group, to provide the corresponding hydrogenated compound of formula:

(I')

wherein W, R^a and R^b are defined as in formula (I).

2. A process according to claim 1, wherein the substrate is hydrogenated in the presence of a complex of formula:

$$[RU(L)_m(L')_wXY] \quad (II)$$

wherein X and Y represent, simultaneously or independently, a hydrogen or chlorine atom, a hydroxy radical, a C₁ to C₆ alkoxy radical or a C₁ to C₆ acyloxy radical;
m is 1 or 2,
wherein w is 1, m is 1; or
wherein w is 0, m is 2;

L represents a bidentate N—P ligand of general formula

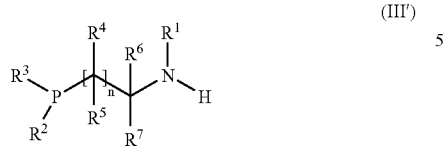

(III')

in which n is an integer from 1 to 3;

R¹ represents a hydrogen atom, a linear, branched or cyclic $C_1$ to $C_6$ alkyl or alkenyl group, possibly substituted;

$R^2$ and $R^3$ represent, simultaneously or independently, a linear, branched or cyclic $C_1$ to $C_6$ alkyl group, possibly substituted, an aromatic ring, possibly substituted; or said groups $R^2$ and $R^2$ being possibly bonded together to form a saturated or aromatic ring having 5 to 6 atoms and including the phosphorous atom to which said $R^2$ and $R^3$ groups are bonded;

$R^4$, $R^5$, $R^6$ and $R^7$ represent, simultaneously or independently, a hydrogen atom, a linear or branched $C_1$ to $C_4$ alkyl group, possibly substituted, or an aromatic ring possibly substituted; or two distinct $R^4$ and/or $R^5$ groups being possibly bonded together to form a $C_5$ to $C_6$ saturated or aromatic ring including the carbon atoms to which each of said $R^4$ or $R^5$ group is bonded;

L' represents a bidentate P—P ligand of formula (IV) wherein $R^2$ and $R^3$ are defined as in formula (III'), and Q represents a linear $C_2$-$C_5$ alkylene radical, possibly substituted, a ferrocenediyl or a biphenyldiyl or binaphthyldiyl radical, possibly substituted; and the possible substituents of $R^1$ to $R^7$ and Q are $C_1$ to $C_5$ alkoxy or polyalkyleneglycol groups, carboxylic esters, $C_1$ to $C_4$ alkyl groups, or $C_5$ to $C_{10}$ cycloalkyl or aromatic groups.

3. A process according to claim 1, wherein the substrate is hydrogenated in the presence of a complex of formula

(II)

wherein X and Y represent, simultaneously or independently, a hydrogen or chlorine atom, a hydroxy radical, a $C_1$ to $C_6$ alkoxy radical or a $C_1$ to $C_6$ acyloxy radical;

m is 1 or 2, wherein w is 1, m is 1; or wherein w is 0, m is 2;

L' represents a bidentate P—P ligand of formula (IV) wherein $R^2$ and $R^3$ are defined below, and Q represents a linear $C_2$-$C_5$ alkylene radical, possibly substituted, a ferrocenediyl or a biphenyldiyl or binaphthyldiyl radical, possibly substituted; and L represents a bidentate N—P ligand of general formula

(III'')

in which G represents a group of formula $R^6C=NR^1$ or a C=N function-containing heterocycle, possibly substituted and possibly containing other heteroatoms;

$R^6$ represents a hydrogen atom, a linear or branched $C_1$ to $C_4$ alkyl group, possibly substituted, or an aromatic ring possibly substituted;

n is an integer from 1 to 3;

$R^1$ represents a hydrogen atom, a linear, branched or cyclic $C_1$ to $C_6$ alkyl or alkenyl group, possibly substituted;

$R^2$ and $R^3$ represent, simultaneously or independently, a linear, branched or cyclic $C_2$ to $C_6$ alkyl group, possibly substituted, an aromatic ring, possibly substituted; or said groups $R^2$ and $R^2$ being possibly bonded together to form a saturated or aromatic ring having 5 to 6 atoms and including the phosphorous atom to which said $R^2$ and $R^3$ groups are bonded;

$R^4$, and $R^5$ represent, simultaneously or independently, a hydrogen atom, a linear or branched $C_1$ to $C_4$ alkyl group, possibly substituted, or an aromatic ring possibly substituted; or two distinct $R^4$ and/or $R^5$ groups being possibly bonded together to form a $C_5$ to $C_6$ saturated or aromatic ring including the carbon atoms to which each of said $R^4$ or $R^5$ group is bonded; and the possible substituents of $R^1$ to $R^6$, Q and G are $C_1$ to $C_5$ alkoxy or polyalkyleneglycol groups, carboxylic esters, $C_1$ to $C_4$ alkyl groups, or $C_5$ to $C_{10}$ cycloalkyl or aromatic groups.

4. A process according to claim 1, wherein the substrate is hydrogenated in the presence of a complex of formula:

(II')

wherein X and Y represent, simultaneously or independently, a hydrogen or chlorine atom, a methoxy, ethoxy or isopropoxy radical, or a $CH_3COO$ or CH3CH₂COO radical; and L is a ligand of formula (V) or (V')

(V)

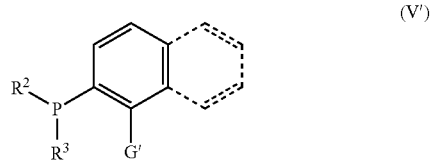

(V')

wherein the dotted lines in formula (V') indicate the presence of a phenyl or a naphthyl group;

b represents 1 or 2;

G' represents a $R^6C=NR^1$ group or a C=N function-containing heterocycle, possibly substituted and possibly containing other heteroatoms;

$R^1$ represents a hydrogen atom or a $C_1$ to $C_4$ linear or branched alkyl group, possibly substituted;

$R^2$ and $R^3$ represent a linear, branched or cyclic $C_2$ to $C_6$ alkyl group or an aromatic ring, possibly substituted;

$R^6$ represents a hydrogen atom, a linear or branched $C_1$ to $C_4$ alkyl group, possibly substituted, or an aromatic ring, possibly substituted; and the possible substituents of $R^1$ to $R^3$, $R^6$ and G' are $C_1$ to $C_5$ alkoxy or polyalkyleneglycol groups, $C_1$ to $C_4$ alkyl groups, or $C_5$ to $C_{10}$ cycloalkyl or aromatic groups.

5. A process according to claim 1, wherein the substrate is hydrogenated in the presence of a complex of formula:

(II')

wherein X and Y represent, simultaneously or independently, a hydrogen or chlorine atom, a methoxy, ethoxy or isopropoxy radical, or a $CH_3COO$ or $CH_3CH_2COO$ radical and L is a ligand of formula (VI) or (VI')

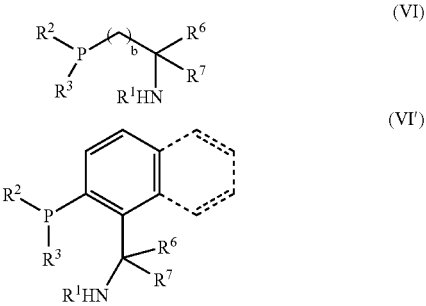

wherein the dotted lines in formula (VI') indicate the presence of a phenyl or a naphthyl group;
$R^1$ represents a hydrogen atom or a $C_1$ to $C_4$ linear or branched alkyl group, possibly substituted;
$R^2$ and $R^3$ represent a linear, branched or cyclic $C_2$ to $C_6$ alkyl group or an aromatic ring, possibly substituted;
b represents 1 or 2;
$R^6$ and $R^7$ represent, simultaneously or independently, a hydrogen atom, a linear or branched $C_1$ to $C_4$ alkyl group, possibly substituted, or an aromatic ring possibly substituted; and
the possible substituents of $R^1$ to $R^3$, $R^6$ and $R^7$ are $C_1$ to $C_5$ alkoxy or polyalkyleneglycol groups, $C_1$ to $C_4$ alkyl groups, $C_5$ to $C_{10}$ cycloalkyl or aromatic groups.

6. A process according to claim 1, wherein the substrate is hydrogenated in the presence of a complex of formula:

$$[Ru(L)_1(L')_1XY] \quad (II'')$$

wherein X and Y represent, simultaneously or independently, a hydrogen or chlorine atom, a methoxy, ethoxy or isopropoxy radical, or a CH3COO or CH3CH2COO radical; and
L' is a bidentate P—P ligand of formula (IV) wherein $R^2$ and $R^3$ represent a linear, branched or cyclic $C_2$ to $C_6$ alkyl group or an aromatic ring, possibly substituted, and Q represents the butane-1,4-diyl radical, possibly substituted, a ferrocenediyl or a binaphthyldiyl radical, possibly substituted;
the possible substituents of the Q group are $C_1$ to $C_5$ alkoxy or polyalkyleneglycol groups, $C_1$ to $C_4$ alkyl groups, or $C_5$ to $C_{10}$ cycloalkyl or aromatic groups; and
L is a ligand of formula (VI) or (VI')

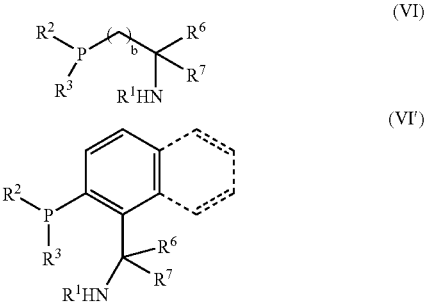

wherein the dotted lines in formula (VI') indicate the presence of a phenyl or a naphthyl group;
$R_1$ represents a hydrogen atom or a $C_1$ to $C_4$ linear or branched alkyl group, possibly substituted;
$R^2$ and $R^3$ are as defined above;
b represents 1 or 2;
$R^6$ and $R^7$ represent, simultaneously or independently, a hydrogen atom, a linear or branched $C_1$ to $C_4$ alkyl group, possibly substituted, or an aromatic ring possibly substituted;
the possible substituents of $R^1$ to $R^3$, $R^6$ and $R^7$ are $C_1$ to $C_5$ alkoxy or polyalkyleneglycol groups, $C_1$ to $C_4$ alkyl groups, $C_5$ to $C_{10}$ cycloalkyl or aromatic groups.

7. A process according to claim 1, wherein the substrate is hydrogenated in the presence of a complex of formula:

$$[Ru(L)_1(L')_1XY] \quad (II'')$$

wherein X and Y represent, simultaneously or independently, a hydrogen or chlorine atom, a methoxy, ethoxy or isopropoxy radical, or a $CH_3COO$ or $CH_3CH_2COO$ radical;
L' is a bidentate P—P ligand of formula (IV) wherein $R^2$ and $R^3$ represent a linear, branched or cyclic $C_2$ to $C_6$ alkyl group or an aromatic ring, possibly substituted, and Q represents the butane-1,4-diyl radical, possibly substituted, a ferrocenediyl or a binaphthyldiyl radical, possibly substituted;
the possible substituents of the Q group are $C_1$ to $C_5$ alkoxy or polyalkyleneglycol groups, $C_1$ to $C_4$ alkyl groups, or $C_5$ to $C_{10}$ cycloalkyl or aromatic groups; and
L is a ligand of formula (V) or (V')

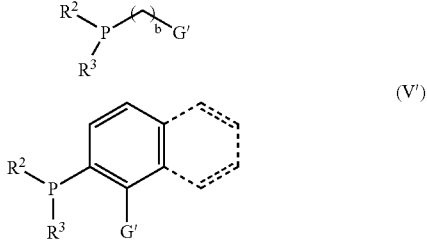

wherein the dotted lines in formula (V') indicate the presence of a phenyl or a naphthyl group;
b represents 1 or 2;
G' represents a $R^6C=NR^1$ group or a $C=N$ function-containing heterocycle, possibly substituted and possibly containing other heteroatoms;
$R^1$ represents a hydrogen atom or a $C_1$ to $C_4$ linear or branched alkyl group, possibly substituted;
$R^2$ and $R^3$ represent a linear, branched or cyclic $C_2$ to $C_6$ alkyl group or an aromatic ring, possibly substituted;
$R^6$ represents a hydrogen atom, a linear or branched $C_1$ to $C_4$ alkyl group, possibly substituted, or an aromatic ring, possibly substituted; and
the possible substituents of $R^1$ to $R^3$, $R^6$ and G' are $C^1$ to $C_5$ alkoxy or polyalkyleneglycol groups, $C_1$ to $C_4$ alkyl groups, or $C_5$ to $C_{10}$ cycloalkyl or aromatic groups.

8. A process according to claim 1, wherein the substrate is hydrogenated in the presence of a complex prepared in situ by reacting an appropriate Ru complex of formula:

$$[Ru(\text{"diene"})(\text{"allyl"})_2]$$

in which "diene" represents a cyclic or linear hydrocarbon containing two carbon-carbon double bonds, conjugated or not, and "allyl" represents a linear or branched $C_3$ to $C_8$ hydrocarbon radical containing one carbon-carbon double bond, with a non-coordinating acid, then treating the resulting solution with the desired amount of a ligand L, and if necessary of ligand L', as defined in claim 1, and finally treating the thus obtained mixture with a base in the presence of a primary or secondary alcohol.

9. A process according to claim 8, wherein the [Ru ("diene")("allyl")$_2$] is [Ru(1,5-cyclooctadiene)(allyl)$_2$] or [Ru(1,5-cyclooctadiene)(methylallyl)$_2$].

10. A process according to claim 1, wherein the substrate is hydrogenated in the presence of a complex prepared in situ by reacting a ruthenium complex of formula [Ru(C$_6$H$_6$)(Cl)$_2$]$_2$ with a required amount of ligand L, and if necessary of ligand L', and then treating the thus obtained reaction mixture with a base, in the presence of an alcohol.

11. A process according to claim 1, wherein the base in the hydrogenation reaction is an organic non-coordinating base, an alkaline or alkaline-earth metal carbonate, a carboxylate salt or an alcoholate or hydroxide salt.

12. A process according to claim 11, wherein the base is an alcoholate or an hydroxide salt selected from the group consisting of the compounds of formula (R$^8$O)$_2$M' or R$^8$OM'' wherein M' is an alkaline-earth metal, M'' is an alkaline metal and R$^8$ stands for hydrogen or a $C_1$ to $C_6$ linear or branched alkyl radical.

13. A process for the reduction of an aryl or diaryl ketone into the corresponding alcohol by hydrogenation, using molecular hydrogen (H$_2$), in the presence of a complex, wherein the complex is of formula:

[Ru(L)$_2$XY]     (II')

wherein L is as ligand of formula (V) or (V') as defined in claim 4; and

X represents a hydrogen atom and Y represents a hydrogen or chlorine atom, a methoxy, ethoxy or isopropoxy radical, or a CH$_3$COO or CH$_3$CH$_2$COO radical; or X and Y represent a hydrogen atom or a CH$_3$COO or CH$_3$CH$_2$COO radical.

14. A process according to claim 1, wherein the hydrogenation is carried out in the absence of a solvent.

15. A process according to claim 1, wherein the hydrogenation is carried out in a primary or secondary alcohol as a solvent.

16. A process according to claim 15, wherein the solvent is ethanol or isopropanol.

17. A process for the reduction of an aryl or diaryl ketone into the corresponding alcohol by hydrogenation, using molecular hydrogen (H$_2$), in the presence of a complex, wherein the complex is of formula:

[Ru(L)$_2$XY]     (II')

wherein L is as ligand of formula (VI) or (VI') as defined in claim 5; and

X represents a hydrogen atom and Y represents a hydrogen or chlorine atom, a methoxy, ethoxy or isopropoxy radical, or a CH$_3$COO or CH$_3$CH$_2$COO radical; or X and Y represent a hydrogen atom or a CH$_3$COO or CH$_3$CH$_2$COO radical.

* * * * *

UNITED STATES PATENT AND TRADEMARK OFFICE
CERTIFICATE OF CORRECTION

PATENT NO. : 7,317,131 B2  
APPLICATION NO. : 10/380483  
DATED : January 8, 2008  
INVENTOR(S) : Rautenstrauch et al.

It is certified that error appears in the above-identified patent and that said Letters Patent is hereby corrected as shown below:

Title Page:
Insert the following before Item (51):
-- (30) Foreign Application Priority Data
Sept. 13, 2000   (WO)................PCT/IB00/01303 --.

Column 21:
Line 33, change "C1 to C8" to -- $C_1$ to $C_8$ --.
Line 53, change "R'" to -- $R^1$ --.
Line 60, after "substituted, or an $OR^{2'}$ or $NR^{2'}R^{3'}$ group," change "$R^2$ and $R^3$" to -- $R^{2'}$ and $R^{3'}$ --.

Column 22:
Line 3, change "$R^5$ or" to -- $R^5$, or --.
Line 7, after "$R^5$ group is bonded; and", start a new paragraph with -- L' represents a bidentate P-P --.

Column 23:
Line 16, change "$C_1$" to -- $C_2$ --.
Line 18, change the second occurrence of "$R^2$" to -- $R^3$ --.

Column 24:
Line 11, change the second occurrence of "$R^2$" to -- $R^3$ --.
Line 32, change "CH3CH2COO" to -- $CH_3CH_2COO$ --.

Column 25:
Line 40, change "CH3COO or CH3CH2COO" to -- $CH_3COO$ or $CH_3CH_2COO$ --.

Column 26:
Line 3, change "R1" to -- $R^1$ --.
Line 60, change "$C^1$" to -- $C_1$ --.

UNITED STATES PATENT AND TRADEMARK OFFICE
CERTIFICATE OF CORRECTION

PATENT NO.       : 7,317,131 B2
APPLICATION NO.  : 10/380483
DATED            : January 8, 2008
INVENTOR(S)      : Rautenstrauch et al.

It is certified that error appears in the above-identified patent and that said Letters Patent is hereby corrected as shown below:

Column 27:
Line 28, change "$R^8OM$" wherein" to -- $R^8OM$", wherein --.

Signed and Sealed this

Sixth Day of May, 2008

JON W. DUDAS
*Director of the United States Patent and Trademark Office*